US006156069A

United States Patent [19]

Amstutz

[11] Patent Number: 6,156,069

[45] Date of Patent: Dec. 5, 2000

[54] PRECISION HIP JOINT REPLACEMENT METHOD

[76] Inventor: Harlan C. Amstutz, 900 Napoli Dr., Pacific Palisades, Calif. 90272

[21] Appl. No.: 09/244,353

[22] Filed: Feb. 4, 1999

[51] Int. Cl.$^7$ ........................................................ A61F 2/32

[52] U.S. Cl. ........................................................ 623/22.11

[58] Field of Search ............................ 623/22, 23, 22.12, 623/22.11, 23.11, 908, 915, 22.15; 606/89, 90, 91, 93, 96

[56] References Cited

U.S. PATENT DOCUMENTS

| | | | |
|---|---|---|---|
| 2,785,673 | 3/1957 | Anderson | 623/23 |
| 3,840,904 | 10/1974 | Tronzo . | |
| 4,101,985 | 7/1978 | Baumann et al. . | |
| 4,123,806 | 11/1978 | Amstutz et al. . | |
| 4,715,860 | 12/1987 | Amstutz et al. . | |
| 4,752,296 | 6/1988 | Buechel et al. . | |
| 4,795,473 | 1/1989 | Grimes | 623/23 |
| 4,846,841 | 7/1989 | Oh | 623/23 |
| 5,037,424 | 8/1991 | Aboczsky . | |
| 5,250,051 | 10/1993 | Maryan . | |
| 5,683,399 | 11/1997 | Jones . | |
| 5,879,404 | 3/1999 | Bateman et al. | 623/22 |
| 5,904,720 | 5/1999 | Farrar et al. | 623/22 |
| 5,980,574 | 11/1999 | Takei et al. | 623/22 |

FOREIGN PATENT DOCUMENTS

| | | | |
|---|---|---|---|
| 1538101 | 7/1968 | France | 623/23 |
| 2406433 | 5/1979 | France | 623/23 |
| 2578739 | 9/1989 | France | 623/23 |
| 2808740 | 6/1979 | Germany | 623/23 |

OTHER PUBLICATIONS

Wright Medical Technology Brochure Entitled "Femoral Surface Replacement System".

*Primary Examiner*—Gene Mancene
*Assistant Examiner*—Eduardo C. Robert
*Attorney, Agent, or Firm*—Oppenheimer Wolff & Donnelly LLP

[57] ABSTRACT

A metal-to-metal surface hip joint replacement method includes the steps of forming a hard metallic spherical femoral surface replacement prosthesis having a central tapered stem and a mating metallic socket prosthesis, with a sphericity tolerance of about one to three microns, a spacing tolerance of about 100 to 300 microns, and slightly greater spacing at the equatorial zone, mounting a centrally located guide pin on the femoral ball or head, using an apertured relocator guide when needed, using a saw cutoff guide with multiple slots for axial adjustments, using a cylindrical starter drill for initial positioning of the drilling of a tapered central opening, and using a tapered guide pin located in the tapered opening for guiding a chamfering step.

23 Claims, 8 Drawing Sheets

FIG. 1
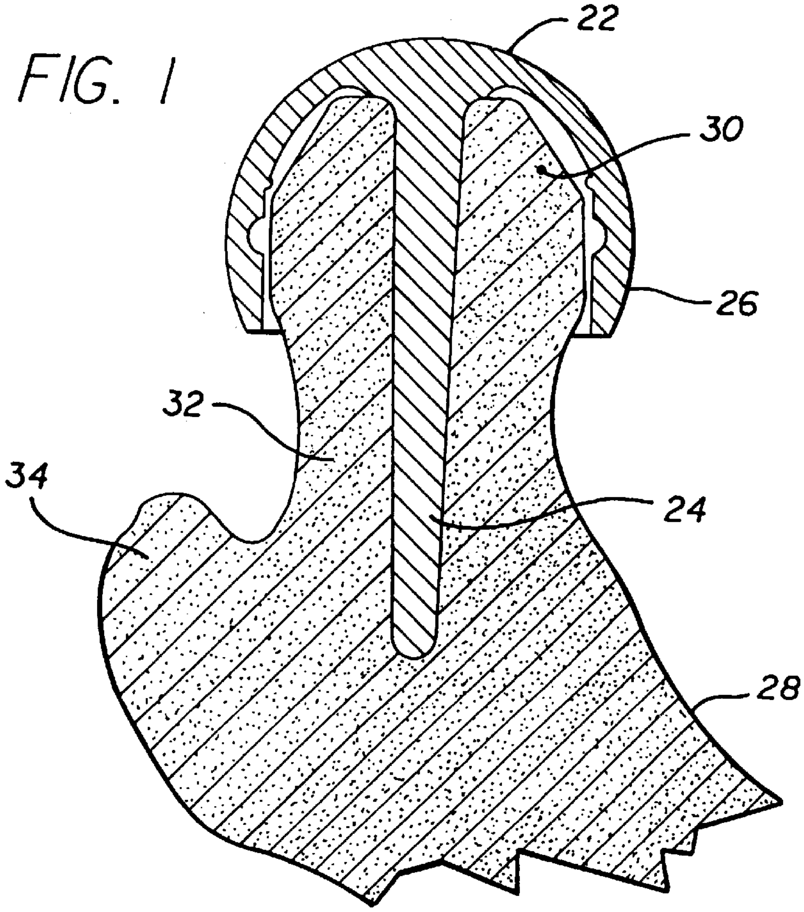
FIG. 2
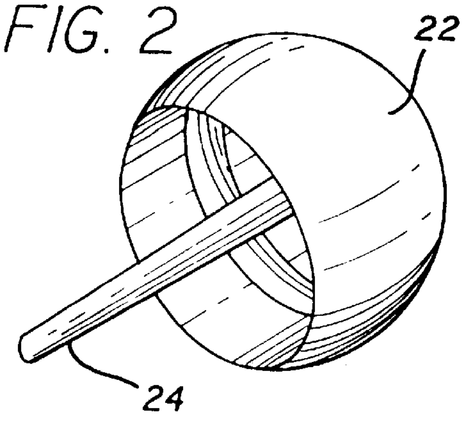
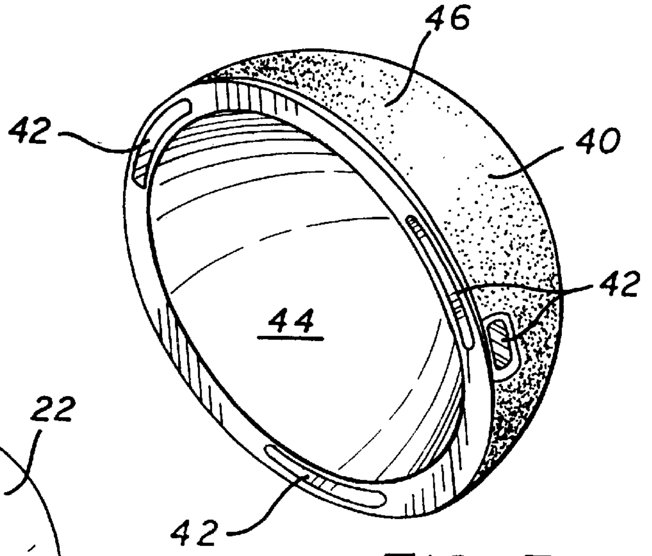
FIG. 3

FIG. 4
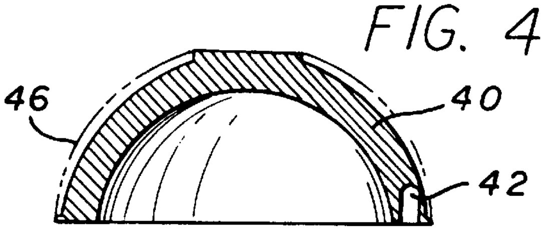
FIG. 5
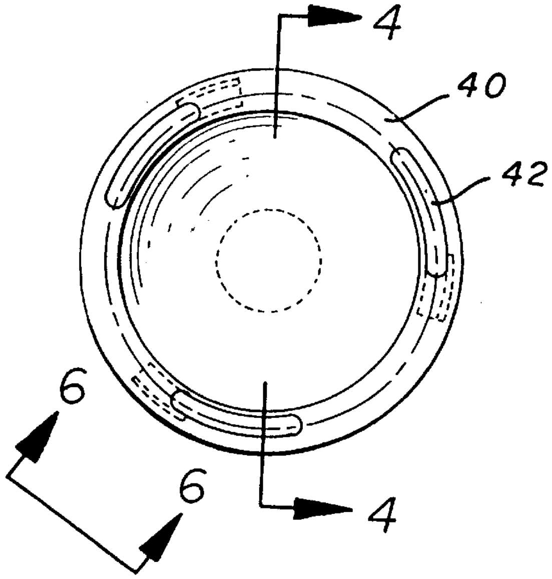
FIG. 6
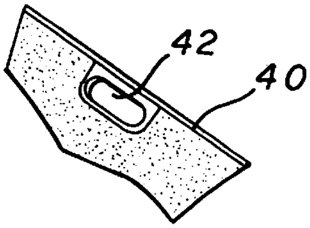
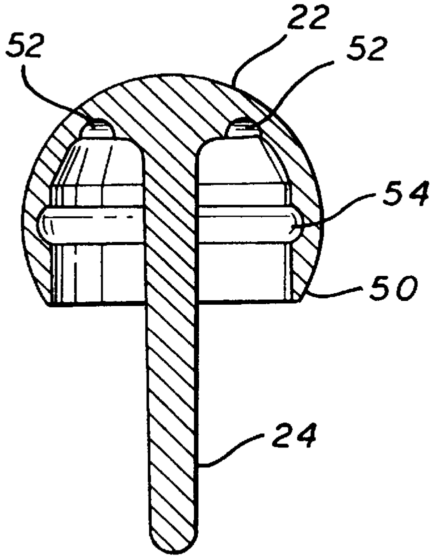
FIG. 7
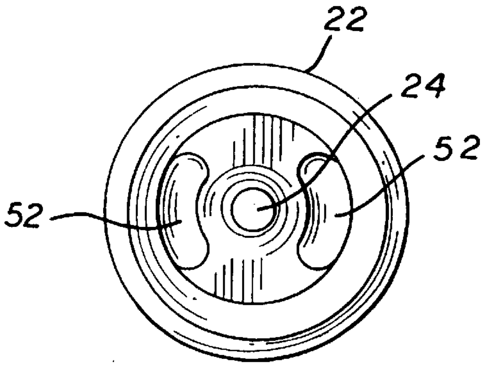
FIG. 8

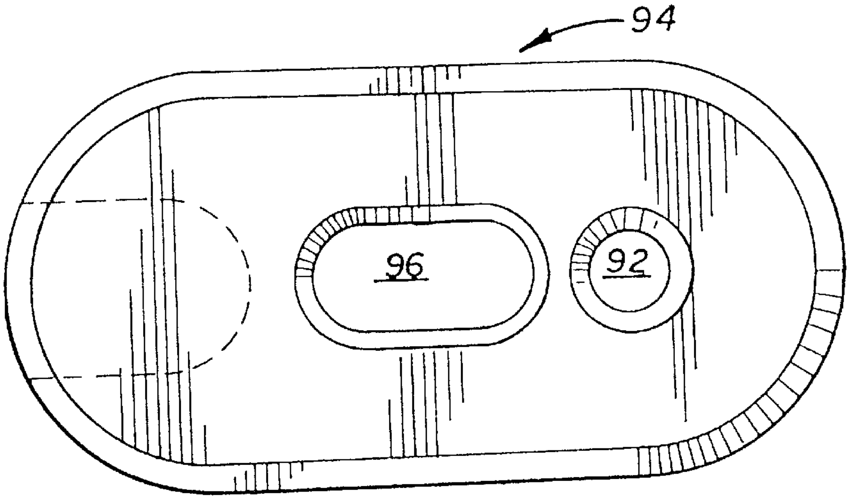
FIG. 11
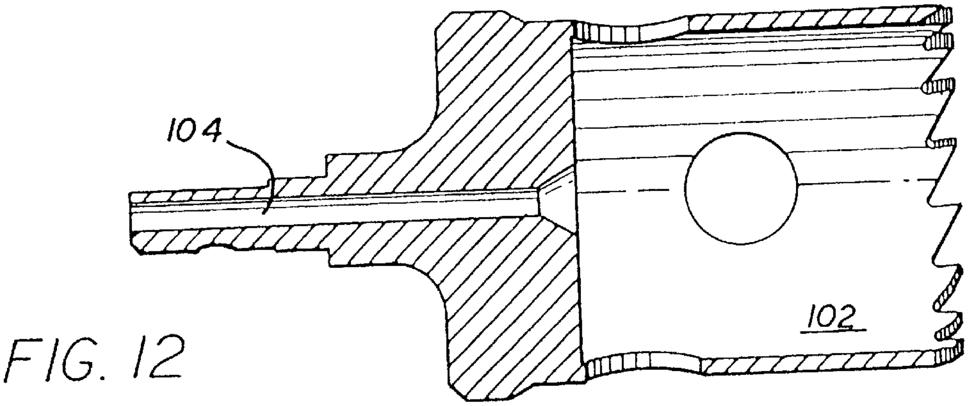
FIG. 12
FIG. 14
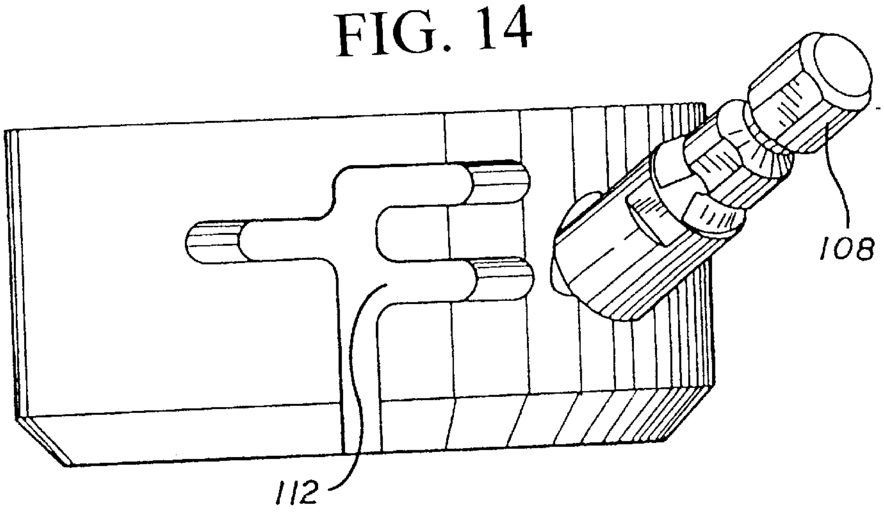

FIG. 13
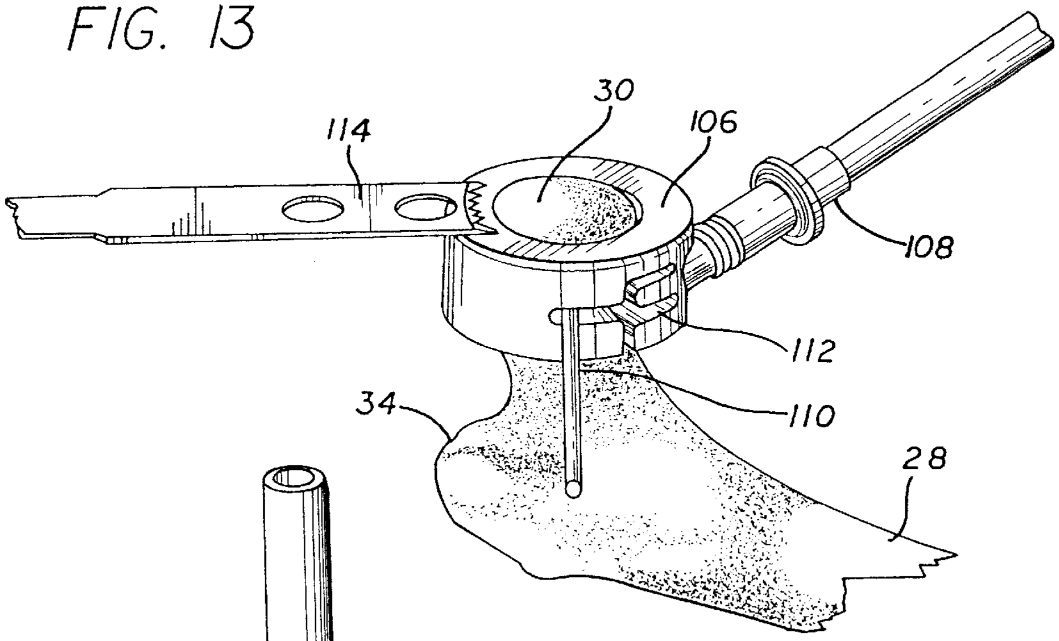
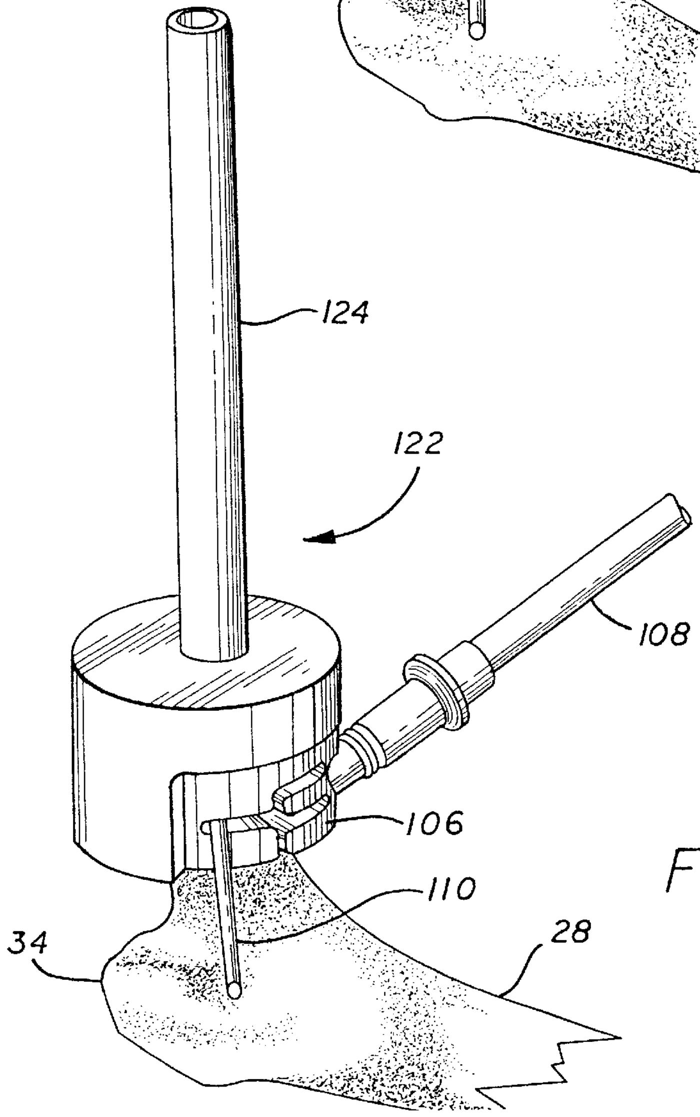
FIG. 15

PRECISION HIP JOINT REPLACEMENT METHOD

FIELD OF THE INVENTION

This invention relates to surface hip joint replacement prostheses.

BACKGROUND OF THE INVENTION

When severe hip joint problems are encountered, it is sometimes necessary to replace the hip joint, either the ball or the socket or both. The large upper leg bone, or femur, has a long lower main portion, with a head or ball connected by a neck portion angled inward toward the hip socket from the upper end of the main portion of the femur.

One generally used hip joint replacement technique involved removal of the head and neck of the femur, and the insertion of a long angled and tapered metal prosthesis into the central "intramedulary" canal at the open upper end of the main straight portion of the femur. This femoral prosthesis typically has a relatively small metal ball at its upper end which mated with small plastic socket mounted on the hip side of the joint.

This "total" hip replacement technique was drastic, involving complete removal of the head and neck of the femur, and made any subsequent hip joint problems difficult to handle.

On the socket side of the joint, referred to as the "acetabular" in medical parlance, some prostheses were employed which used a plastic cup to mate with the femoral component; and it has been determined that these plastic acetabular components were subject to considerable wear, producing particulate matter which adversely affected the lifetime of the hip joint prosthesis. Metal-to-metal joints were also proposed in the 1960s, but lack of accuracy in sphericity and other problems had prevented their wide acceptance.

As shown in U.S. Pat. No. 4,123,806, granted Nov. 7, 1978, an early femoral prosthesis involved a cobalt-chromium-molybdenum metallic shell of generally hemispherical shape, designed on the principle of removing all non-viable femoral head bone, but also preserving as much of the head and neck as possible. A polyethylene socket or acetabular component was employed. The femoral shell was cemented onto the head of the femur, following shaping to one of several standard sizes. This surface replacement conserved bone and permitted a full femoral hip replacement if problems arose with initial replacement prosthesis. However, in several cases the polyethyl-ethylene wear and resultant particulate material caused loosening of the femoral shell and/or the acetabular shell.

In a more recent prior art development, as described in a publication entitled "Femoral Surface Replacement System, Surgical Technique," a metal-to-metal hip joint prosthesis has been employed, using a relatively thin all-metal socket prosthesis secured in place by bone-ingrowth; and a cemented metal shell as the femoral component. The metal shell femoral component was provided with a central tapered stem extending centrally from the shell into the femoral neck for a distance slightly less than the diameter of the shell.

However, the results have, on occasion, not been quite as good as would be desirable, and occasional problems have arisen with regard to accurately positioning the femoral shell, and providing the very uniform layer of cement between the femoral head and the metal shell, which is desirable for firm securing and long life of the prosthesis and/or for preventing notching of the neck which could lead to femoral neck fracture.

It is also noted that metal-to-metal hip joint prosthesis have been tried heretofore, but have not been entirely satisfactory, with clicking and ratcheting noises occurring in some cases, and with the potential increased torque causing loosening.

Further, in some cases, the original length of the leg has not been maintained, with prior art prostheses which have been employed.

Concerning one other prior art prosthesis involving surface configurations on the prosthesis stem for encouraging bone ingrowth, and no cement on the stem, the result was secure fixation of the stem, but atrophy of the bone around the outer periphery of the femoral head.

SUMMARY OF THE INVENTION

In accordance with a specific method for forming a durable surface hip replacement prosthesis, illustrating the principles of the invention, the method may include the following steps: (a) forming a hard metal acetabular, or socket, component which is thin and has a highly accurate hemispherical configuration with "polar" and "equatorial" or rim areas with slightly greater than spherical dimensions; (b) forming a metal shell femoral component with a central stem extending from the shell for a distance slightly less than the diameter of the shell, and a highly accurate outer surface, generally spherical but with increased "polar" and "equatorial" tolerances relative to said socket component; (c) mounting a guide pin centered on the femoral ball or head, and extending toward the center of the femoral neck, checking the pin location using a feeler gauge, and accurately re-locating the pin using an apertured relocation guide; (d) reaming the outer surface of the femoral head to a cylindrical configuration using the pin as a guide, and mounting a multiply slotted adjustable saw cut-off guide on a second, laterally extending guide pin with the pin in the selected slot providing an accurate saw cutoff location to mate with the femoral shell prosthesis; (e) forming an accurately centered tapered central hole in the femoral head, using a tower guide secured to the saw cut-off guide, a cylindrical starter drill, and a tapered drill accurately positioned by the starter drill hole; (f) using a tapered guide pin in the tapered central hole, chamfering the outer corners of the cylindrically shaped femoral head, to mate with the femoral shell prosthesis; and (g) securing the femoral shell prosthesis in place using an even layer of cement on the accurately positioned mating surfaces of the prosthesis and the femoral head. The tapered guide pin of step (f) is also advantageously employed with a transparent plastic cup shaped member mounted on the pin, to check the modified configuration of the femoral head to assure uniform relatively small spacing between the femoral shell prosthesis and the femoral head, to receive a uniform layer of cement.

It is further noted that the cumulative effect of the improved techniques as enumerated in the preceding paragraph is to provide a more reliable step-by-step procedure resulting in consistently accurately positioned prostheses, which have a uniform, even layer of cement between the femoral shell and the femoral head, without misalignment, and producing a durable, artificially surfaced joint. It is also noted that the individual new steps and techniques included in the foregoing paragraph may be employed separately or as part of a surgical hip joint procedure using other steps to accomplish similar results.

One advantage of the revised prosthesis configuration is that slight deformation of either or both the socket or acetabular prosthesis, or the femoral shell prosthesis, near their rims, which may occur during the operative procedure, are accommodated without problems.

Concerning another aspect, the use of the relocator fixture facilitates accurate re-location of the initial Steinman pin, so that central alignment with the femoral head and neck may be more readily accomplished.

The additional location slots in the cut-off guide permit ready re-adjustment of the axial position of the cut-off guide to more accurately and optimally conform to the configuration of the femoral shell prosthesis, while removing non-viable bone at the outer end of the femoral head. Similarly, by guiding the chamfering step using an accurately and firmly positioned tapered guide pin, mounted in the tapered central hole, the shape of the femoral head is formed to more accurately conform to the inner shell shape.

Further, the problem of possible inaccurate location of the tapered hole as it is drilled using an unguided, long tapered drill, is obviated by the use of a fully guided cylindrical starter drill.

It is noted in passing that the foregoing specific method steps are particularly helpful in successfully providing a durable hip joint replacement under relatively difficult conditions with very limited access to the operating site.

The use of relatively close tolerances in the metal-to-metal joint, preferably with slightly increased equatorial spacing, has eliminated the clicking and/or ratcheting noises previously encountered, and reduces surface wear, thereby providing a durable prosthesis.

However, in some cases with patients with a very active lifestyle and good femoral bone structure apart from the joint surfaces, a cementless femoral shell could be employed. The femoral shell would have a smooth stem but with the inner surface of the shell being formed of the sintered beads preferably of a cobalt chrome alloy, for encouraging bone growth and fixation. The shell would make an interference fit with the outer reamed surface of the femoral head; and the recesses shown in the present drawings would not be present. With this cementless femoral method, the statements made in the present specification relative to cement would, of course, not be applicable.

Other objects, features and advantages of the invention will become apparent from a consideration of the following detailed description, and from the accompanying drawings.

BRIEF DESCRIPTION OF THE DRAWINGS

FIG. 1 is a cross-sectional view of a metallic femoral surface replacement prosthesis prior to cement fixation;

FIGS. 2 and 3 are perspective views of the mating femoral ball (head) and acetabular (socket) prostheses employed in the implementation of the present invention;

FIGS. 4, 5 and 6 are detailed views showing the construction of the metallic acetabular prosthesis;

FIGS. 7 and 8 are cross-sectional and bottom plan views, respectively, of the femoral prosthesis;

FIG. 11 is a plan view of an apertured pin relocation guide for use in relocating the central guide pin;

FIG. 12 is a cross-sectional view of a cylindrical reamer for forming the sides of the femoral head into a cylindrical configuration;

FIG. 13 shows a cutoff guide for guiding the cutoff saw;

FIG. 14 is an enlarged side view of the cutoff guide, with multiple positioning slots;

FIG. 15 shows the addition of a hollow tower guide mounted on the saw cutoff guide;

DETAILED DESCRIPTION OF THE PREFERRED TECHNIQUE

Figure 9:
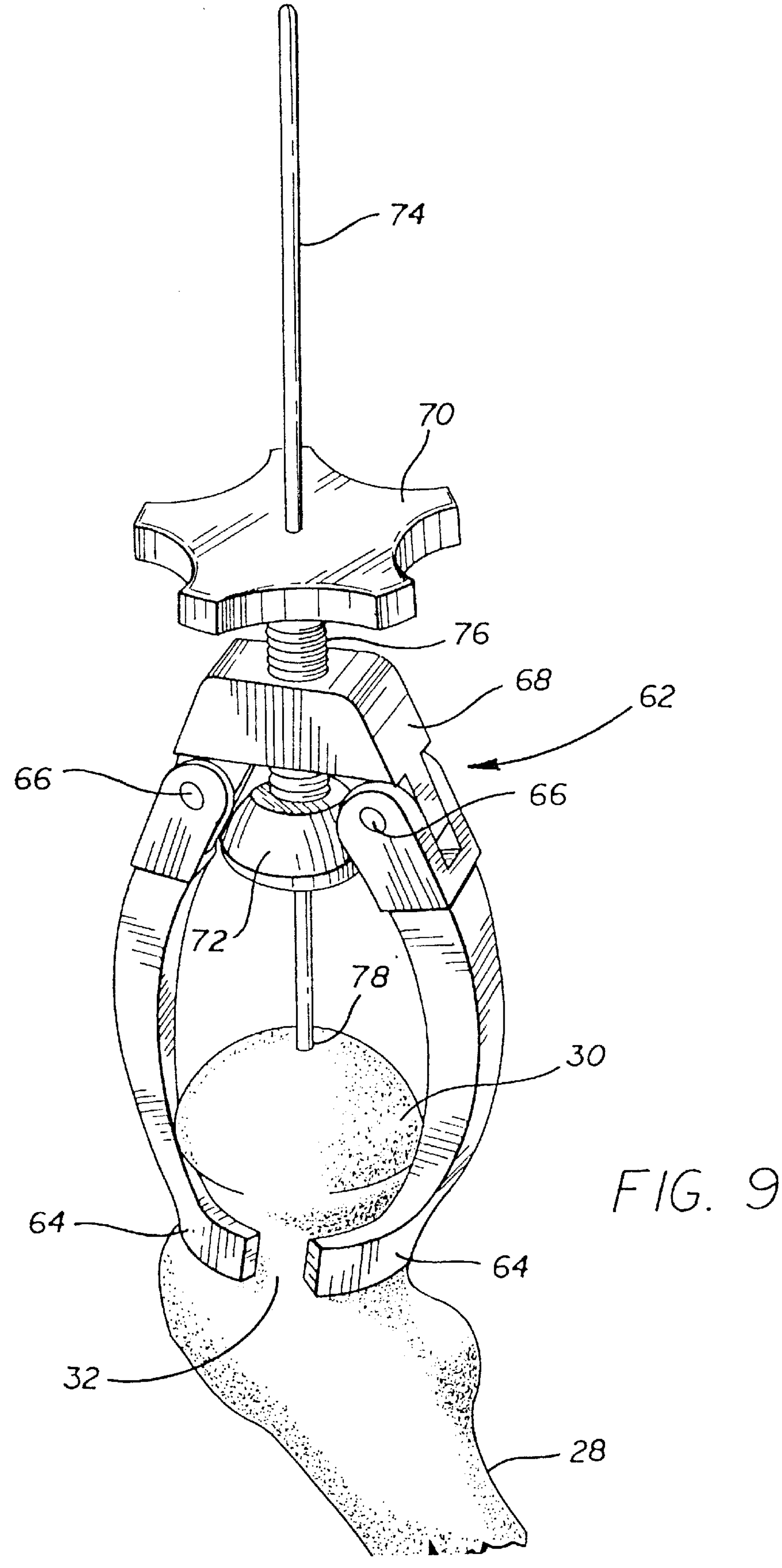
FIG. 9 is a perspective view of a guide clamp which is secured onto the neck of the femur to locate a guide pin for the cylindrical reaming of the femoral head.

Referring more particularly to the drawings, FIG. 1 shows a cross-sectional view of a hard metallic femoral prosthesis at 22 of the surface replacement type. The femoral prostheses 22 includes a central tapered stem 24 and a spherical surface replacement portion 26. The prosthesis is shown mounted on the upper end of the femur 28, or thigh-bone, which is the large upper leg bone. The upper portion of the femur 28 includes a head or ball portion 30, a neck 32, and the trochanter 34. Incidentally, the trochanter is a boney protuberance from the femur to which major muscle groups are secured for controlling the motion of the leg, for example. In certain prior femoral surface replacement procedures, the trochanter was removed to give more access for the operating procedure, and subsequently reattached; however, using the present surgical techniques, this undesired step is no longer involved.

Returning to the femoral prosthesis 22, it has an extent which is slightly greater than a hemisphere to cover all of the reamed bone of the femoral head, and the central tapered stem 24 extends from the center of the spherical shell 26 into the head and neck of the femur beyond the lower edge or skirt of the prosthesis a distance slightly greater than the distance from the upper end of the prosthesis 22 to the edge of the skirt.

The prosthesis 22 is made of known high strength biologically inert metallic materials such as a cobalt chrome alloy.

FIGS. 2 and 3 of the drawings arc prospective views of the femoral prosthesis 22, and the acetabular or socket prosthesis 40. Regarding the acetabular prosthesis 40, at its edges it includes openings 42 to which tooling may be secured in order to mount the acetabular prosthesis in place, and on rare occasions to remove it. The prosthesis 40 has an outer surface which is formed of fine granular sintered material, preferably of a cobalt chrome alloy of a known type, which encourages bone ingrowth. It is approximately ½ centimeter or 5 millimeters in thickness. The interior surface 44 of the acetabular component 40 is generally spherical in its configuration. The spherical surface 44 mates with the outer spherical surface configuration of the femoral prosthesis 22, with a tolerance of between one and five microns or preferably between one and two or three microns, where a micron is equal to one one-thousandth of a millimeter (0.001 mm). The very accurate machining or grinding of the outer surface of the femoral component 22 and the inner surface 44 of the acetabular component are very useful in the use of the metal-to-metal prosthesis as described in the present specification. The clearance between the femoral and the acetabular components is preferably about 125 to 250 microns, with larger size assemblies having larger tolerances. This spacing permits lubrication of the surfaces by the patient's normal synovial fluid. These accurately machined prostheses are available in successive sizes ranging from 36 to 54 millimeters, in two millimeter increments, from Wright Medical Technology, Inc., 5677 Airline Road, Arlington, Tenn. 38002. The surgical equipment disclosed in this specification may also be purchased from Wright Medical Technology, Inc.

FIGS. 4, 5 and 6 are detailed mechanical drawings of the acetabular or socket prosthesis 40. Disclosed in FIGS. 4, 5 and 6 is the preferred configuration of the securing openings 42, and also the location of the sintered beads 46 which are on the outer surface of the hemispherical configuration of the prosthesis 40.

FIGS. 7 and 8 are cross-sectional and lower plan views, respectfully, of the femoral prosthesis 22. The femoral prosthesis 22 includes the outer spherical surface 26 which extends for somewhat more than a hemisphere, and has a lower edge or skirt 50. Within the femoral prosthesis 22 are recesses 52 which tend to resist rotation of the prosthesis once it is secured in place with cement. In addition, the circular recess 54 is useful for resisting axial shifting of the position of the femoral prosthesis once it is cemented in place.

It may be noted that the lower edge of the acetabular component is subject to fairly high stresses on occasion, in view of the mechanical securing of the prosthesis to tooling for securing it in place. Similarly, in view of the thin nature of the lower edge 50 of the femoral prosthesis, it too may be subject to stresses. Accordingly, with the tolerance over the greater portion of the mating areas of the two prosthesis being relatively small, in the neighborhood of one to three or five microns, the tolerance in the equatorial or lower areas of the two prostheses is somewhat greater, so that slight deflections or minor distortions of the lower edges of either of the two prostheses will not adversely affect the operation of the artificial hip joint. In some cases the tolerances at the "polar" area of the prostheses may also be increased, due to manufacturing methods.

Referring now to FIG. 9 of the drawings, a clamp 62 is provided with jaws 64 which grip the neck 32 of the femur 28, between the head 30 of the femur and the main portion of the femoral bone. The two jaws 64 of the clamp 62 are pivoted at points 66 to the support member 68 so that when the handle 70 is rotated and the camming surface 72 is moved upwardly, the clamp jaws 64 forcibly engage the neck 32 of the femur. A Steinman pin 74 is advanced through openings in the handle 70, the threaded actuator 76 and the camming member 72 and enters the head 30 of the femur at point 78, hopefully centrally and axially aligned with the head 30 and the neck 32 of the femur.

Figure 10:
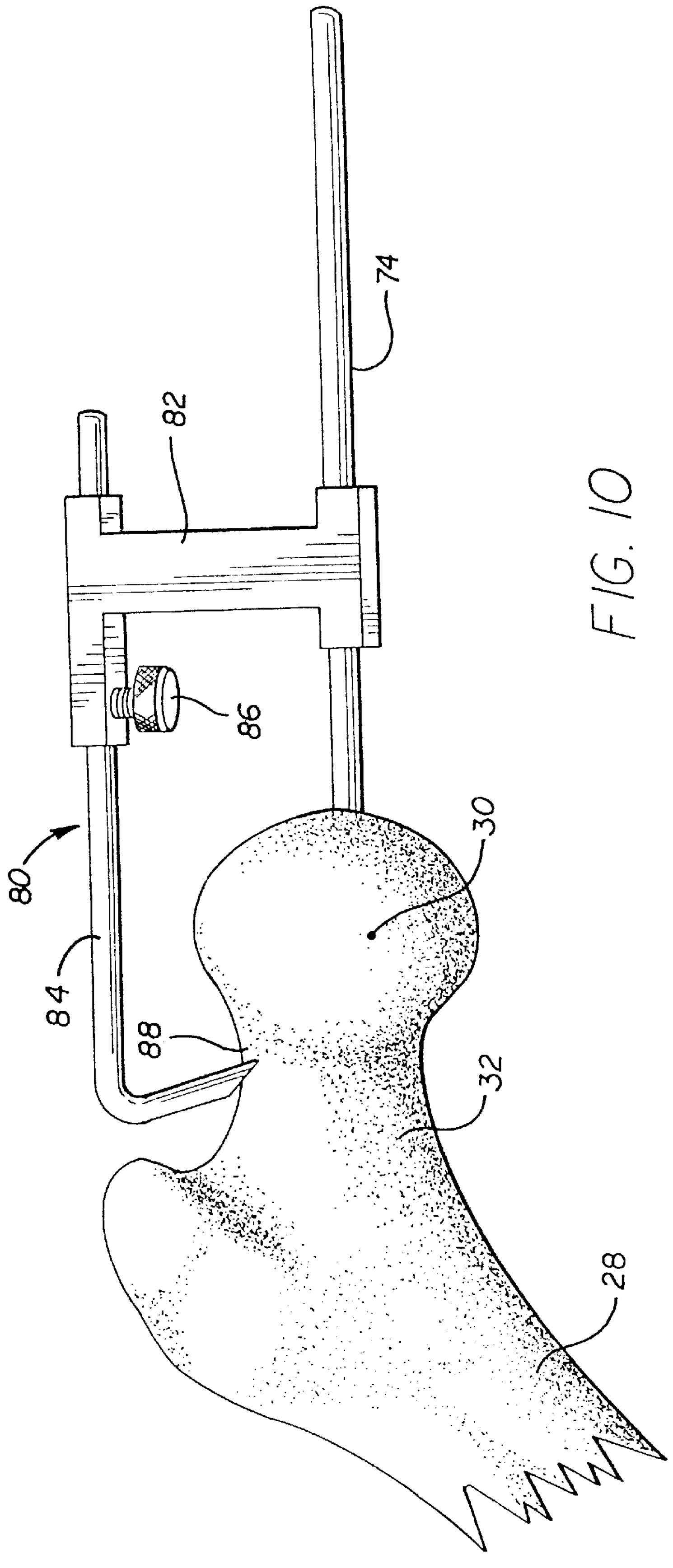
FIG. 10 shows a gauge for initial checking of the central location of the guide pin.

Referring now to FIG. 10 of the drawings, the central and axially location of the Steinman pin 74 relative to the head 30 and neck 32 of the femur is checked. More specifically, the feeler gauge 80 includes the arm 82 pivotally mounted on the Steinman pin 74, and also includes the wire member 84 held in place in an opening in the support 82 by the set screw 86. As the gauge assembly is rotated around the head and neck of the femur, the variations of the point 88 on the surface of the neck 32 of the femur, will indicate how accurately the Steinman pin 74 is located in the head of the femur.

In the past, there have been some occasions when the Steinman pin has not been as accurately located as would be desirable, in view of the spacing from the clamp 62 as shown in FIG. 9 to the point 78 of entry into the head 30 of the femur. With misalignment, the next step, which is to be cylindrical reaming, could be shifted from its optimal location in alignment with the central axis of the femoral head and neck. In the event that the location of the Steinman pin 74, as checked out by the gauge 80, as shown in FIG. 10, is not accurate, a relocation fixture such as that shown in FIG. 11 may be employed. Specifically, with substantial deviations from proper alignment, the opening 92 in the relocation fixture 94 may be slid over the Steinman pin 74 with the fixture 94 mounted against the head of the femur. Then, a correctly located Steinman pin 74 may be inserted into the head of the femur through the larger opening 96, which permits changing of the angle of the Steinman pin 74 as well as its location. In the event that a smaller shift in position is all that is required, the opening 96 may be slipped over the Steinman pin 74 and a new Steinman pin shifted slightly in position may be secured through the opening 96.

FIG. 12 shows a cylindrical reamer 102 which is now utilized, with the Steinman pin 74, now accurately positioned, extending through the opening 104 of the reamer assembly 102. Using this reamer 102, the outer surface of the femoral head 30 is reconfigured to a cylindrical shape.

The next step, as shown in FIG. 13, is to employ a cutoff guide 106, which may be held in position using the handle 108 secured to the cutoff guide 106. It may be noted that a second Steinman pin 110 is mounted to extend out laterally from the cylindrical surface of the femoral head. The slot configuration 112 is now employed to locate the cutoff guide in the proper axial position on the cylindrical surface of the femoral head 30. The desired axial position is chosen in order to permit the removal of non-viable bone from the upper end of the femoral head 30. Following proper positioning of the saw cutoff guide, the saw 114 is actuated to form a flat upper surface on the femoral head 30. An enlarged side view of the saw cutoff guide 106 is provided in FIG. 14 of the drawings.

Figure 16:
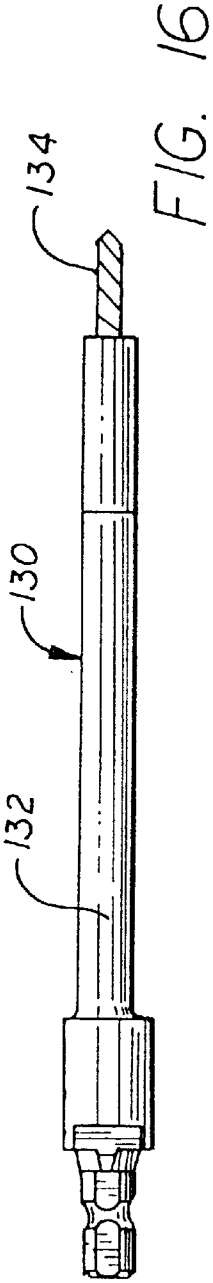
FIG. 16 shows a starter drill for initial positioning of the tapered hole in the femoral head.

The next step is indicated in FIG. 15 and involves mounting the tower guide 122 onto the saw cutoff guide 106. Following securing of this tower guide in place, the drill shown in FIG. 16 is employed, using the long vertical tube 124 of the tower guide as an alignment mechanism. It may be noted that the drill 130 of FIG. 16 has a long cylindrical portion 132, and a very short small drill portion 134 at its outer end. With this configuration, a starter hole in the upper end of the flattened femoral head may be formed accurately aligned with the axis of the cylindrical head without significant departure from this axis.

Figure 17:
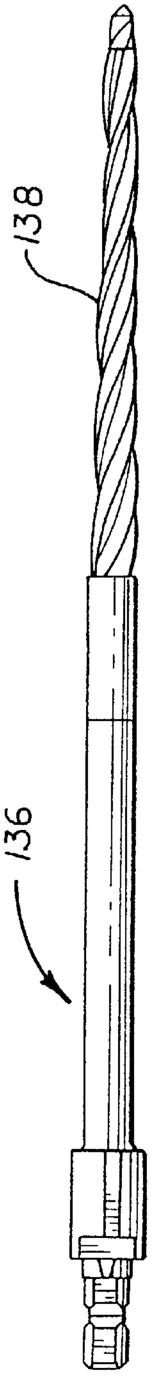
FIG. 17 is a side view of the tapered drill.
Figure 18:
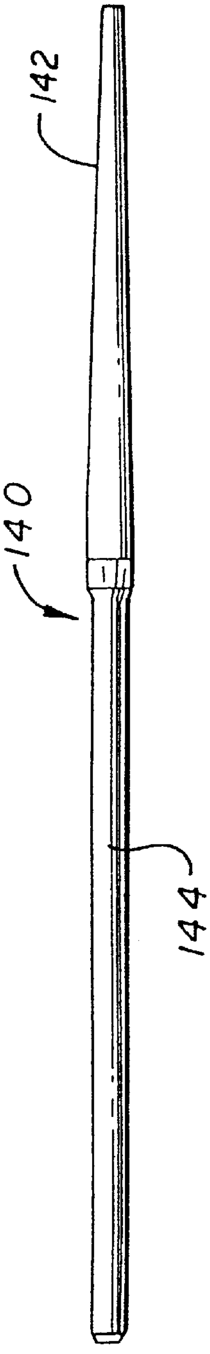
FIG. 18 is a tapered guide pin which is sized to precisely fit in the tapered hole formed by the drill of FIG. 17.

The next step is to complete a tapered hole into the head and neck of the reconfigured upper end of the femur 30 (see FIG. 1) using the tapered drill 136 as shown in FIG. 17, with the tapered drill portion 138 forming a hole which is initially aligned by virtue of the accurately positioned hole prepared by the drill 130 of FIG. 16. In this regard it may be noted that it had been proposed previously to use the tapered drill 136, as shown in FIG. 17, without the use of a starter drill such as that shown in FIG. 16. However, it was found that misalignment or inaccuracy in positioning occurred because the long tapered drill could be angled to one side so that true axial positioning was not consistently obtained. Accordingly, the use of the drill 130 as shown in FIG. 16 has eliminated a problem which previously occurred.

FIG. 16 shows a guide pin 140 having a tapered portion 142 which is precisely the same shape as the drill 138 which formed the opening. With the tapered portion 142 inserted into the hole drilled by the drill 138, an accurately and firmly positioned guide pin 144, protruding from the upper flat surface of the reconfigured femoral head, is obtained.

Figure 19:
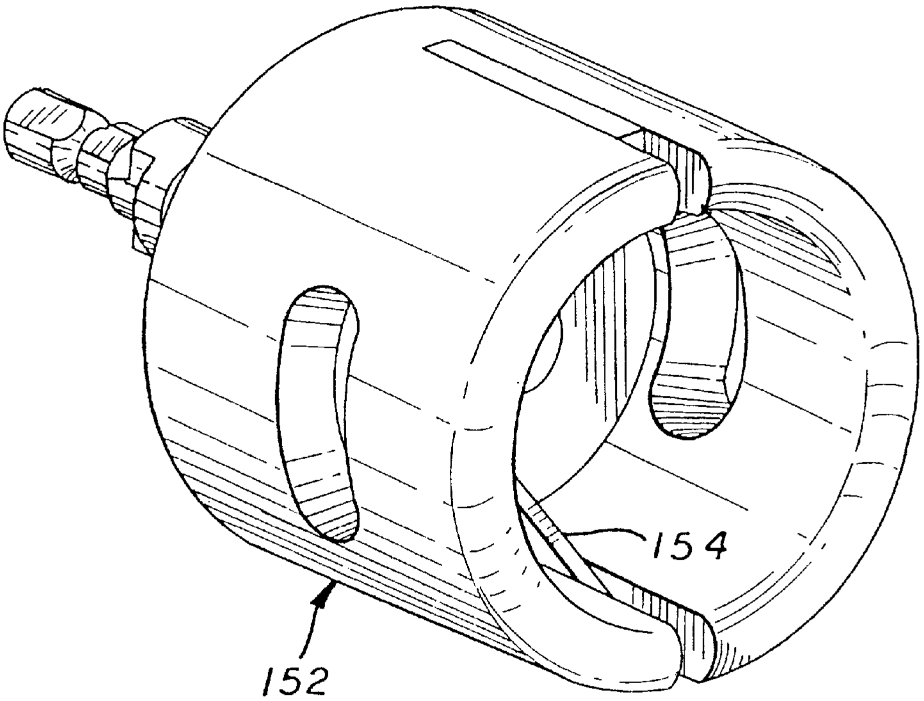
FIG. 19 is a chamfer cutter which chamfers the corners of the femoral head, and is guided by the pin of FIG. 18.

Referring now to FIG. 19, with the pin 140 in position, the chamfering tool 152, with its cutting blade 154, is used to chamfer the corners of the femoral head. The result is the configuration of the femoral head as shown in FIG. 1 of the drawings.

Figure 20:
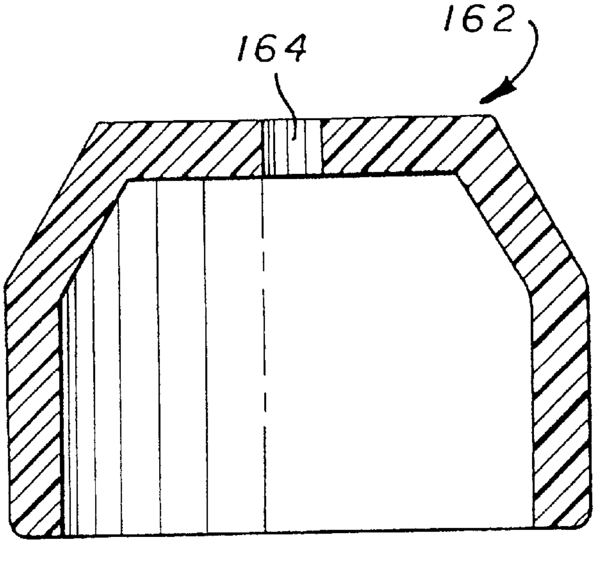
FIG. 20 is a transparent plastic gauge which is mounted on the guide pin to check clearance around the shaped femoral head for the reception of a uniform thickness layer of cement.

Following chamfering, the transparent guide 162, as shown in FIG. 20, is mounted on the guide pin, with the guide pin portion 144 extending through the opening 164 in the configuration checking plastic cup member 162. When the cup member 162 is in position, there should be a small even spacing around the sides of the cup so that following the application of cement, a uniform layer of cement will be present between the femoral component and the reconfigured femoral head.

Following this checking step, a smooth even coating of permanent cement of a known bio-compatible type is applied to the interior of the femoral prosthesis 22 and to the stem 24, and the prosthesis 22 is mounted onto the head of the femur, and pressed firmly down to make a tight fit. Excess cement is removed from the lower periphery of the skirt 50 of the prosthesis where it is adjacent to the head 30 and neck 32 of the femur.

The acetabular or socket prosthesis makes an interference with the reamed opening formed to receive it; and the tooling which engages the openings 42 is employed to maintain alignment as it is forced into place.

In closing, the foregoing detailed description relates to preferred apparatus and techniques illustrating the principles of the invention. However, various modifications and modified procedures are considered to be within the scope of the invention. Thus, by way of example and not of limitation, somewhat different apparatus such as a pin relocator fixture having multiple holes, or a saw cutoff guide with multiple holes, or threaded components to shift its outer surface, or slightly different clamps, reamers or chamfering tooling could be employed, without departing from the spirit and scope of the invention. Similarly, a tower guide may be directly secured to the cylindrical shaped femoral head instead of being secured to the cutoff guide. Accordingly, the present invention is not limited to the precise apparatus as shown in the drawings, or to the precise technique as described in the foregoing specification.

What is claimed is:

1. A precision hip joint replacement method involving a metallic femoral surface replacement prosthesis and a metallic acetabular surface replacement prosthesis for a femur having a main body portion and a ball or head coupled to the upper end of the main portion of the femur by a neck, said head and neck having a center and a central axis, said femoral head having an outer surface and an extreme outer end, and said prosthesis having a lower edge, said method comprising the steps of:

a.) forming a hard metallic spherical surface replacement prosthesis, with an extent slightly greater than a hemisphere, and with a central tapered stem;

b.) forming both an entirely metallic acetabular socket prosthesis and said metallic surface replacement femoral head prosthesis with a high degree of spherical accuracy and tolerances, but with slightly increased spacing tolerance at the equatorial zone of each said prostheses;

c.) mounting a guide pin centered on the femoral ball, or head, and extending toward the center of the neck joining the ball to the upper end of the main portion of the femur;

d.) using a feeler gauge to check the alignment of the guide pin with the axis of the femoral neck;

e.) relocating the pin to the center of the axis of the femoral neck using an apertured relocation guide;

f.) reaming the outer surface of the femoral head to a cylindrical configuration using the centrally mounted pin as a guide;

g.) mounting a saw cutoff guide extending around the femoral head, with said saw cutoff guide having a plurality of laterally extending slots with a lateral guide pin extending from said head through a selected one of said slots, to axially locate said cutoff guide;

h.) using a saw and said cutoff guide, cut off the extreme outer end of the femoral head thereby forming outer corners of the cylindrically formed head;

i.) mounting a tower guide on said saw cutoff guide;

j.) using a cylindrical drill, bore a starter hole for the stem of the metallic replacement femoral prostheses;

k.) using a tapered drill matching the shape of the femoral prosthesis stem and said starter hole, bore a tapered hole to a measured depth into the head and neck of the femur;

l.) inserting a tapered guide pin into the tapered hole;

m.) using the tapered guide pin for alignment, chamfer the outer corners of the cylindrically formed femoral head thereby completing the formation of the exposed modified surface of the femoral head;

n.) mounting a guide gauge on said tapered guide pin and checking for a uniform small clearance for cement all the way around the modified surface of said femoral head; and o.) applying cement to the exposed modified surface of said femoral head and within the femoral prosthesis, and mounting the femoral prosthesis on the femoral head and removing excess cement following seating of the femoral prosthesis;

whereby an even layer of cement is located between said femoral prosthesis and the outer surface of said femoral head, when the tapered stem of said prosthesis is fitted down into said tapered hole, and said cement seals the lower edge of said prosthesis around the modified head and the adjacent neck of the femur.

2. A method as defined in claim 1 wherein the sphericity tolerances of said acetabular and femoral prostheses is between one and three microns over most of the mating surfaces of said prostheses.

3. A method as defined in claim 1 wherein said prostheses have central polar zones and mating surfaces, and wherein the spacing tolerance at the polar zone of said prostheses is slightly greater than the spacing tolerance on most of the mating surfaces of said prostheses.

4. A method as defined in claim 1 wherein said acetabular prosthesis is formed with a plurality of recesses in its edge, for holding said prosthesis during the positioning of said prosthesis.

5. A precision hip joint replacement method involving a metallic femoral surface replacement prosthesis and a metallic acetabular surface replacement prosthesis for a femur having a main body portion and a ball or head coupled to the upper end of the main portion of the femur by a neck, said head and neck having a center and a central axis, said femoral head having an outer surface and an extreme outer end, and said prosthesis having a lower edge, said method comprising the steps of:

a.) forming a hard metallic spherical surface replacement prosthesis, with an extent slightly greater than a hemisphere, and with a central tapered stem;

b.) forming both an entirely metallic acetabular socket prosthesis and said metallic surface replacement femoral head prosthesis with a high degree of spherical accuracy and tolerances, but with slightly increased spacing tolerance at the equatorial zone of each said prosthesis, wherein the sphericity tolerance of said acetabular and femoral prostheses is between one and five microns over most of the mating surfaces of said prostheses;

c.) mounting a guide pin centered on the femoral ball, or head, and extending toward the center of the neck joining the ball to the upper end of the main portion of the femur;

d.) reaming the outer surface of the femoral head to a cylindrical configuration using the centrally mounted pin as a guide;

e.) mounting a saw cutoff guide extending around the femoral head;

f.) using a saw, cut off the extreme outer end of the femoral head thereby forming outer corners of the cylindrically formed head;

g.) mounting a tower guide on said femoral head;

h.) using a tapered drill matching the shape of the femoral prosthesis stem, boring a tapered hole to a measured depth into the head and neck of the femur;

i.) using a centrally located guide pin for alignment, chamfering the outer corners of the cylindrically formed femoral head; and j.) firmly mounting the femoral prosthesis on the femoral head.

6. A method as defined in claim 5 including providing a plurality of interconnected slots in said cutoff guide, and fixing said cutoff guide in a selected slot to guide cutting off the outer end of said femoral ball to match the configuration of the femoral prosthesis.

7. A method as defined in claim 5 wherein said prostheses have central polar zones and mating surfaces, and wherein the spacing tolerance at the polar zone of said prostheses is slightly greater than the spacing tolerance on most of the mating surfaces of said prostheses.

8. A precision hip joint replacement method as defined in claim 5 wherein the mounting of said saw cutoff guide includes using a saw cutoff guide having a plurality of spaced openings with a guide pin extending laterally from said femoral head through a selected one of said openings, to accurately position said cutoff guide.

9. A precision hip joint replacement method as defined in claim 8 wherein the mounting of said saw cutoff guide involves the use of openings in the form of interconnected parallel slots.

10. A precision hip joint replacement method as defined in claim 5 further including the steps of using a feeler gauge to check the alignment of the guide pin with the central axis of the femoral head and neck, and relocating the pin to the center of said central axis using an apertured relocator guide.

11. A precision hip joint replacement method as defined in claim 10 wherein said relocating step includes the use of a relocator guide having a first generally circular opening for receiving said guide pin, and a second opening which is substantially larger than said first opening.

12. A precision hip joint replacement method as defined in claim 5 including the step of boring a starter hole for the stem of the femoral prosthesis using a drill which is cylindrical over most of its length, aligned by said tower guide, prior to boring the tapered hole.

13. A precision hip joint replacement method as defined in claim 5 including the step of using a tapered guide pin mounted in said tapered hole as a guide for said chamfering step.

14. A precision hip joint replacement method as defined in claim 5 including the additional steps of mounting a tapered guide pin in said tapered hole, and checking the modified configuration of said femoral head by using a transparent plastic cup shaped member having the shape of the femoral prosthesis without the stem, and verifying the configuration of the femoral head for receiving the femoral prosthesis.

15. A precision hip joint replacement method involving a metallic femoral surface replacement prosthesis and a metallic acetabular surface replacement prosthesis for a femur having a main body portion and a ball or head coupled to the upper end of the main portion of the femur by a neck, said head and neck having a center and a central axis, said femoral head having an outer surface and an extreme outer end, and said prosthesis having a lower edge, said method comprising the steps of:

a.) forming a hard metallic spherical surface replacement prosthesis, with an extent slightly greater than a hemisphere, and with a central tapered stem;

b.) mounting a guide pin centered on the femoral ball, or head, and extending toward the center of the neck joining the ball to the upper end of the main portion of the femur;

c.) using a feeler gauge to check the alignment of the guide pin with the axis of the femoral stem;

d.) relocating the pin to the center of the axis of the femoral neck using an apertured relocation guide;

e.) reaming the outer surface of the femoral head to a cylindrical configuration using the centrally mounted pin as a guide;

f.) mounting a saw cutoff guide extending around the femoral head;

g.) using a saw, cut off the extreme outer end of the femoral head; mounting a tower guide on said saw cutoff guide thereby forming outer corners of the cylindrically formed head;

h.) using a cylindrical drill, bore a starter hole for the stem of the metallic replacement femoral prosthesis;

i.) using a tapered drill matching the shape of the femoral prosthesis stem, bore a tapered hole to a measured depth into the head and neck of the femur;

j.) insert a tapered guide pin into the tapered hole;

k.) using the tapered guide pin for alignment, chamfer the outer corners of the cylindrically formed femoral head;

l.) mounting a guide gauge on said tapered guide pin and verifying the configuration of the femoral head for receiving the femoral prosthesis; and m.) firmly mounting the femoral prosthesis on the femoral head.

16. A method as defined in claim 15 including providing a plurality of interconnected slots in said cutoff guide, and fixing said cutoff guide in a selected slot to guide cutting off the outer end of said femoral ball to match the configuration of the femoral prosthesis.

17. A method as set forth in claim 15 wherein said forming step includes forming both an entirely metallic acetabular socket prosthesis and said metallic surface replacement femoral head prosthesis with a high degree of spherical accuracy and tolerances, but with slightly increased spacing tolerances at the equatorial zone of said prostheses.

18. A method as defined in claim 17 wherein said prostheses have central polar zones and mating surfaces, and wherein the spacing between said acetabular and femoral prostheses is between one hundred and three hundred microns over most of the mating surfaces of said prostheses.

19. A method as defined in claim 17 wherein said prostheses have central polar zones and mating surfaces, and wherein the spacing tolerance at the polar zone of said prostheses is slightly greater than the spacing tolerance on most of the mating surfaces of said prostheses.

20. A precision hip joint replacement method involving a metallic femoral surface replacement prosthesis and a metallic acetabular surface replacement prosthesis for a femur having a main body portion and a ball or head coupled to the upper end of the main portion of the femur by a neck, said head and neck having a center and a central axis, said femoral head having an outer surface and an extreme outer end, and said prosthesis having a lower edge, said method comprising the steps of:

a.) forming a hard metallic spherical surface replacement prosthesis, with an extent slightly greater than a hemisphere, and with a central tapered stem;

b.) forming both an entirely metallic acetabular socket prosthesis and said metallic surface replacement femoral head prosthesis with a high degree of spherical accuracy and tolerances;

c.) mounting a guide pin centered on the femoral ball, or head, and extending toward the center of the neck joining the ball to the upper end of the main portion of the femur;

d.) using a feeler gauge to check the alignment of the guide pin with the axis of the femoral stem;

e.) relocating the pin to the center of the axis of the femoral neck using an apertured relocation guide;

f.) reaming the outer surface of the femoral head to a cylindrical configuration using the centrally mounted pin as a guide;

g.) mounting a saw cutoff guide extending around the femoral head;

h.) using a saw, cut off the extreme outer end of the femoral head thereby forming outer corners of the cylindrically formed head;

i.) mounting a tower guide on said femoral head;

j.) using a tapered drill matching the shape of the femoral prosthesis stem, boring a tapered hole to a measured depth into the head and neck of the femur;

k.) using a centrally located guide pin for alignment, chamfering the outer corners of the cylindrically formed femoral head; and l.) firmly mounting the femoral prosthesis on the femoral head.

21. A precision hip joint replacement method involving a metallic femoral surface replacement prosthesis and a metallic acetabular surface replacement prosthesis for a femur having a main body portion and a ball or head coupled to the upper end of the main portion of the femur by a neck, said head and neck having a center and a central axis, said femoral head having an outer surface and an extreme outer end, and said prosthesis having a lower edge, said method comprising the steps of:

a.) forming a hard metallic spherical surface replacement prosthesis, with an extent slightly greater than a hemisphere, and with a central tapered stem;

b.) forming both an entirely metallic acetabular socket prosthesis and said metallic surface replacement femoral head prosthesis with a high degree of spherical accuracy and tolerances;

c.) mounting a guide pin centered on the femoral ball, or head, and extending toward the center of the neck joining the ball to the upper end of the main portion of the femur;

d.) reaming the outer surface of the femoral head to a cylindrical configuration using the centrally mounted pin as a guide;

e.) mounting a saw cutoff guide extending around the femoral head, with said saw cutoff guide having a plurality of laterally extending slots with a lateral guide pin extending through a selected one of said slots, to axially locate said cutoff guide;

f.) using a saw, cut off the extreme outer end of the femoral head thereby forming outer corners of the cylindrically formed head;

g.) mounting a tower guide on said femoral head;

h.) using a tapered drill matching the shape of the femoral prosthesis stem, boring a tapered hole to a measured depth into the head and neck of the femur;

i.) using a centrally located guide pin for alignment, chamfering the outer corners of the cylindrically formed femoral head; and j.) firmly mounting the femoral prosthesis on the femoral head.

22. A precision hip joint replacement method involving a metallic femoral surface replacement prosthesis and a metallic acetabular surface replacement prosthesis for a femur having a main body portion and a ball or head coupled to the upper end of the main portion of the femur by a neck, said head and neck having a center and a central axis, said femoral head having an outer surface and an extreme outer end, and said prosthesis having a lower edge, said method comprising the steps of:

a.) forming a hard metallic spherical surface replacement prosthesis, with an extent slightly greater than a hemisphere, and with a central tapered stem;

b.) forming both an entirely metallic acetabular socket prosthesis and said metallic surface replacement femoral head prosthesis with a high degree of spherical accuracy and tolerances;

c.) mounting a guide pin centered on the femoral ball, or head, and extending toward the center of the neck joining the ball to the upper end of the main portion of the femur;

d.) reaming the outer surface of the femoral head to a cylindrical configuration using the centrally mounted pin as a guide;

e.) mounting a saw cutoff guide extending around the femoral head;

f.) using a saw, cut off the extreme outer end of the femoral head thereby forming outer corners of the cylindrically formed head;

g.) mounting a tower guide on said femoral head;

h.) using a cylindrical drill guided by said tower guide, bore a starter hole for the stem of the metallic replacement femoral prostheses;

i.) using a tapered drill matching the shape of the femoral prosthesis stem, boring a tapered hole located by said starter hole to a measured depth into the head and neck of the femur;

j.) using a centrally located tapered guide pin for alignment, chamfering the outer corners of the cylindrically formed femoral head; and k.) firmly mounting the femoral prosthesis on the femoral head.

23. A precision hip joint replacement method involving a metallic femoral surface replacement prosthesis and a metallic acetabular surface replacement prosthesis for a femur having a main body portion and a ball or head coupled to the upper end of the main portion of the femur by a neck, said head and neck having a center and a central axis, said femoral head having an outer surface and an extreme outer end, and said prosthesis having a lower edge, said method comprising the steps of:

a.) forming a hard metallic spherical surface replacement prosthesis, with an extent slightly greater than a hemisphere, and with a central tapered stem;

b.) forming both an entirely metallic acetabular socket prosthesis and said metallic surface replacement femoral head prosthesis with a high degree of spherical accuracy and tolerances;

c.) mounting a guide pin centered on the femoral ball, or head, and extending toward the center of the neck joining the ball to the upper end of the main portion of the femur;

d.) reaming the outer surface of the femoral head to a cylindrical configuration using the centrally mounted pin as a guide;

e.) mounting a saw cutoff guide extending around the femoral head;

f.) using a saw, cut off the extreme outer end of the femoral head thereby forming outer corners of the cylindrically formed head;

g.) mounting a tower guide on said femoral head;

h.) using a tapered drill matching the shape of the femoral prosthesis stem, boring a tapered hole to a measured depth into the head and neck of the femur;

i.) insert a tapered guide pin into said tapered hole;

j.) using said tapered guide pin for alignment, chamfering the outer corners of the cylindrically formed femoral head; and k.) firmly mounting the femoral prosthesis on the femoral head.

* * * * *

UNITED STATES PATENT AND TRADEMARK OFFICE
Certificate

Patent No. 6,156,069 Patented: December 5, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Harlan C. Amstutz, Pacific Palisades, CA (US); Albert L. Lippincott III, Prior Lake, MN (US); and Carlos E. Gil, Collierville, TN (US).

Signed and Sealed this Twelfth Day of October 2010.

EDUARDO C. ROBERT
*Supervisory Patent Examiner*
Art Unit 3733
Technology Center 3700